US012684067B1

(12) United States Patent
Winston et al.

(10) Patent No.: US 12,684,067 B1
(45) Date of Patent: Jul. 14, 2026

(54) MEDICAL PREFERENCE BASED INTERACTIVE VOICE RESPONSE COMMUNICATION CONFIGURATION

(71) Applicant: West Corporation, Omaha, NE (US)

(72) Inventors: Michelle Winston, Omaha, NE (US);
Nancy Bergantzel, Castle Rock, CO (US); Graeme Dean, Live Oak, FL (US); Charles McGavren, Omaha, NE (US); Jim Milroy, Omaha, NE (US);
Matt Panaccione, Pepperell, MA (US);
Prabha Sundaram, Salt Lake City, UT (US)

(73) Assignee: West Technology Group, LLC,
Omaha, NE (US)

( * ) Notice: Subject to any disclaimer, the term of this patent is extended or adjusted under 35 U.S.C. 154(b) by 0 days.

(21) Appl. No.: 15/672,923

(22) Filed: Aug. 9, 2017

(51) Int. Cl.
| | |
|---|---|
| *G06F 3/0481* | (2022.01) |
| *G16H 10/60* | (2018.01) |
| *H04M 3/493* | (2006.01) |
| *H04M 3/51* | (2006.01) |
| *G16H 10/00* | (2018.01) |

(52) U.S. Cl.
CPC ............ *H04M 3/493* (2013.01); *G16H 10/60* (2018.01); *H04M 3/5166* (2013.01); *G06F 3/0481* (2013.01); *G16H 10/00* (2018.01); *H04M 2203/655* (2013.01)

(58) Field of Classification Search
CPC ............... H04M 3/493; H04M 3/1566; H04M 2203/655; H04M 3/5166; G06F 19/32; G06F 319/32; G16H 10/00; G16H 10/60

USPC .......................................................... 715/753
See application file for complete search history.

(56) References Cited

U.S. PATENT DOCUMENTS

| | | | | | |
|---|---|---|---|---|---|
| 6,094,635 | A | * | 7/2000 | Scholz .................... | G10L 15/26 |
| | | | | | 704/270 |
| 6,594,347 | B1 | * | 7/2003 | Calder .................. | H04M 3/493 |
| | | | | | 379/88.01 |
| 8,694,331 | B2 | * | 4/2014 | DeBelser ............ | G06F 19/3468 |
| | | | | | 705/2 |
| 10,496,793 | B1 | | 12/2019 | Lawrence et al. | |
| 2003/0149751 | A1 | * | 8/2003 | Bellinger ................ | H04L 67/51 |
| | | | | | 709/220 |
| 2004/0098253 | A1 | * | 5/2004 | Balentine ................ | G10L 15/22 |
| | | | | | 704/215 |

(Continued)

OTHER PUBLICATIONS

U.S. Appl. No. 15/672,954, filed Aug. 9, 2017 Michelle Mason Winston.

*Primary Examiner* — Tuyetlien T Tran

(57) ABSTRACT

Automated patient care may include a patient accessing and registering to receive ongoing care from automated services. Third parties may also be notified regarding a patient's ongoing care services. One example method of operation may include identifying a patient case profile, identifying a number of contacts associated with the patient case profile, identifying a trigger in the patient case file and a number of preferences, linking a number of patient requirements identified in the patient case profile with the number of contacts and preferences responsive to identifying the trigger, creating a number of communication instances each having a date and a communication medium, and transmitting notifications to the number of contacts and at least one designated patient device identified by the preferences.

16 Claims, 11 Drawing Sheets

(56) References Cited

U.S. PATENT DOCUMENTS

| | | | | |
|---|---|---|---|---|
| 2005/0177788 A1* | 8/2005 | Snyder | .................. | G06F 40/151 |
| | | | | 715/234 |
| 2009/0003549 A1* | 1/2009 | Baird | ................... | H04M 3/493 |
| | | | | 379/88.18 |
| 2009/0216558 A1* | 8/2009 | Reisman | ................ | G16H 40/67 |
| | | | | 705/3 |
| 2010/0082391 A1 | 4/2010 | Soerensen et al. | | |
| 2011/0202370 A1* | 8/2011 | Green, III | ............. | G16H 10/60 |
| | | | | 705/3 |
| 2011/0301982 A1* | 12/2011 | Green, Jr. | ............. | G16H 40/67 |
| | | | | 705/3 |
| 2012/0143013 A1* | 6/2012 | Davis, III | ............. | G16H 50/20 |
| | | | | 600/300 |
| 2013/0065569 A1* | 3/2013 | Leipzig | .................. | H04W 8/22 |
| | | | | 455/416 |
| 2013/0124226 A1* | 5/2013 | Gedala | ................... | G16H 10/60 |
| | | | | 705/3 |
| 2013/0262135 A1 | 10/2013 | Nichols et al. | | |
| 2014/0244285 A1* | 8/2014 | Hinkle | .................. | G16H 50/20 |
| | | | | 705/2 |
| 2015/0127358 A1* | 5/2015 | Porter | ................... | G16H 40/20 |
| | | | | 705/2 |
| 2015/0242582 A1 | 8/2015 | Mehta et al. | | |
| 2015/0302150 A1* | 10/2015 | Mazar | ................... | G16H 40/63 |
| | | | | 705/2 |
| 2016/0110507 A1* | 4/2016 | Abbo | .................. | G06F 16/2465 |
| | | | | 705/3 |
| 2016/0117471 A1* | 4/2016 | Belt | ....................... | G16H 20/10 |
| | | | | 705/2 |
| 2016/0323217 A1 | 11/2016 | Subramani et al. | | |
| 2017/0262604 A1 | 9/2017 | Francois | | |
| 2018/0286502 A1* | 10/2018 | Lane | ...................... | G16H 50/20 |

* cited by examiner

100

220

250

500

MEDICAL PREFERENCE BASED INTERACTIVE VOICE RESPONSE COMMUNICATION CONFIGURATION

TECHNICAL FIELD

This application relates to providing medical care assistance to patients and more particularly to a patient procedure follow-up configuration which enables various communication platforms and third party assistance to measures to manage the patients.

BACKGROUND

A patient at a medical facility may have undergone surgery, have a chronic condition and may require ongoing care, follow-up information, medications, visits, etc. For every patient appointment, admission, post-operation schedule, prescription, etc., there exists some data file record of such events. Patient care follow-up is conventionally a process of identifying certain necessary measures and attempting to combine those measures as subsequent patient care options. However, the likelihood is low that the patient undergoes all such necessary subsequent measures and in a manner conducive to the patient's preferences and availability.

SUMMARY

One example embodiment may include a method that includes at least one of identifying a patient case profile, identifying a plurality of contacts associated with the patient case profile, identifying a trigger in the patient case file and a plurality of preferences, linking a plurality of patient requirements identified in the patient case profile with the plurality of contacts and preferences responsive to identifying the trigger, creating a plurality of communication instances each comprising at least one date and at least one communication medium, d transmitting notifications to the plurality of contacts and at least one designated patient device identified by the plurality of preferences.

Another example embodiment may include an apparatus that includes a processor configured to identify a patient case profile, identify a plurality of contacts associated with the patient case profile, identify a trigger in the patient case file and a plurality of preferences, link a plurality of patient requirements identified in the patient case profile with the plurality of contacts and preferences responsive to identifying the trigger, create a plurality of communication instances each comprising at least one date and at least one communication medium, and a transmitter configured to transmit notifications to the plurality of contacts and at least one designated patient device identified by the plurality of preferences.

Still another example embodiment may include a non-transitory computer readable storage medium configured to store instructions that when executed causes a processor to perform identifying a patient case profile, identifying a plurality of contacts associated with the patient case profile, identifying a trigger in the patient case file and a plurality of preferences, linking a plurality of patient requirements identified in the patient case profile with the plurality of contacts and preferences responsive to identifying the trigger, creating a plurality of communication instances each comprising at least one date and at least one communication medium, and transmitting notifications to the plurality of contacts and at least one designated patient device identified by the plurality of preferences.

Still a further example embodiment may include identifying a trigger in a patient case file associated with a patient that matures on a particular date, identifying a plurality of contacts required to satisfy the trigger, creating a plurality of communication instances each comprising at least one communication medium based on one or more preferences associated with the plurality of contacts, and transmitting notifications to the plurality of contacts and at least one designated patient device identified by the plurality of preferences.

Yet still a further example embodiment may include an apparatus that includes a processor configured to identify a trigger in a patient case file associated with a patient that matures on a particular date, identify a plurality of contacts required to satisfy the trigger, create a plurality of communication instances each comprising at least one communication medium based on one or more preferences associated with the plurality of contacts, and a transmitter configured to transmit notifications to the plurality of contacts and at least one designated patient device identified by the plurality of preferences.

Still yet another example embodiment may include a non-transitory computer readable storage medium configured to store instructions that when executed causes a processor to perform identifying a trigger in a patient case file associated with a patient that matures on a particular date, identifying a plurality of contacts required to satisfy the trigger, creating a plurality of communication instances each comprising at least one communication medium based on one or more preferences associated with the plurality of contacts, and transmitting notifications to the plurality of contacts and at least one designated patient device identified by the plurality of preferences.

DETAILED DESCRIPTION

It will be readily understood that the instant components, as generally described and illustrated in the figures herein, may be arranged and designed in a wide variety of different configurations. Thus, the following detailed description of the embodiments of a method, apparatus, and system, as represented in the attached figures, is not intended to limit the scope of the application as claimed, but is merely representative of selected embodiments.

The instant features, structures, or characteristics of described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" has been used in the description of embodiments, the application may be applied to many types of network data, such as, packet, frame, datagram, etc. The term "message" also includes packet, frame, datagram, and any equivalents thereof. Furthermore, while certain types of messages and signaling are depicted in exemplary embodiments they are not limited to a certain type of message, and the application is not limited to a certain type of signaling.

According to example embodiment, patients may subscribe to continual service for post-procedure care from doctors, caregivers and/or any party with an interest in the patient's well-being. A patient case study of a particular patient that is deemed to be 55 years old and experiencing certain health concerns may require an admission to a medical facility (i.e., hospital). The pre-admission care may include a retinal exam, an overnight visit, etc. Next, a thoracentesis procedure is performed with imaging along with a hemodialysis. The hospital admission is then identified as a four-day visit. Lastly, the post-discharge care is identified as including a visit, an x-ray, a pneumonia condition and a set of prescriptions. A patient in this example may have multiple instances of follow-up with the medical care center (i.e., hospital, primary care office, elderly care facility, home care operations, etc.). Additionally, there may be mandatory actions necessary to ensure patient health stability and post-procedure healing/care.

Figure 1:
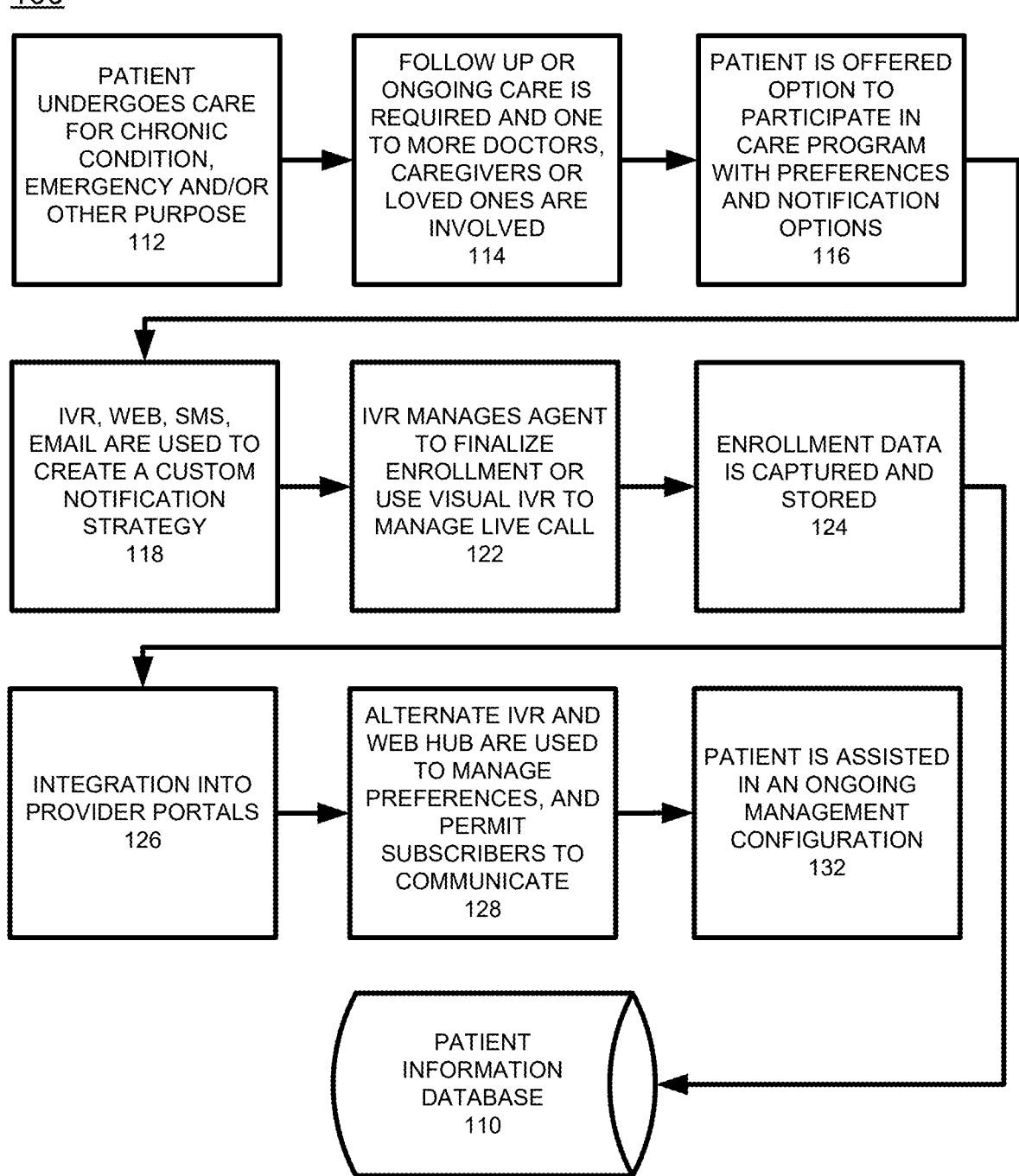
FIG. 1 illustrates a logic diagram of an overview of patient care enrollment according to an example embodiment.

FIG. 1 illustrates a logic diagram of an overview of patient care enrollment according to an example embodiment. Referring to FIG. 1, in the event that the patient has undergone one or more hospital related procedures the patient may be contacted via one or more patient user devices to setup, establish and enroll in the comprehensive care program offered by the present software application according to example embodiments. This process may invoke patient information, third party care information, including but not limited to known care givers, physicians, medical staff, emergency contacts, service providers, etc.

In FIG. 1, the patient may have undergone a procedure, appointment, hospital visit, etc. 112. Follow-up or ongoing care 144 is determined to be required based on one or more existing requirements. The requirements may be flags included in the patient profile. For example, after a surgery, a patient may be required to have blood work, suture checks and other follow-up appointments which must occur within 2-4 weeks of the surgical procedure. The flag may be a trigger which enables the application to launch, create an appointment date and invoke resources. An example of invoking resources may include at least one physician, at least one medical assistant, at least one emergency contact, etc., all of which must be notified of the upcoming date. The flag may be a parameter [F] that requires at least one physician parameter [P1], at least one emergency contact parameter [EC1], at least one appointment date [AD1] and one or more patient preference parameters [PP1, PP2 . . . . PPN] (e.g., phone call, text message, email, etc.). The need to create the appointment may invoke all such parameters which are linked to notification modules, integration modules and other modules which could effectively begin with a need for an appointment and result in multiple notifications being sent to various parties, a calendar entry being created, a prescription being filled, etc.

Continuing with the example in FIG. 1, the patient is offered an option to participate in the patient care application program and enter various preferences on how to be contacted, how to communicate with caregivers, physicians, etc., when to be notified, the types of care preferred, etc. 116. The interactive voice response system over the Internet (visual IVR) or phone (voice IVR), web based application, or short message service communication mediums can be used to communicate with the patient on his or her mobile device or other computing device having a processor, display and memory 118. For this example, the communication will be performed over some type of IVR system. The IVR manages agent activity to finalize the enrollment 122. The enrollment data submitted by the patient or those assisting the patient is received and stored in a patient file 124. The various parties involved in the patient care customization process may be notified and reached by establishing custom provider portals 126. The alternate IVR and web hub systems are used to manage the preferences, updates and permit the subscriber to communication 128. The patient is then assisted in ongoing management 132. All patient information is stored in a patient databank 110.

Figure 2A:
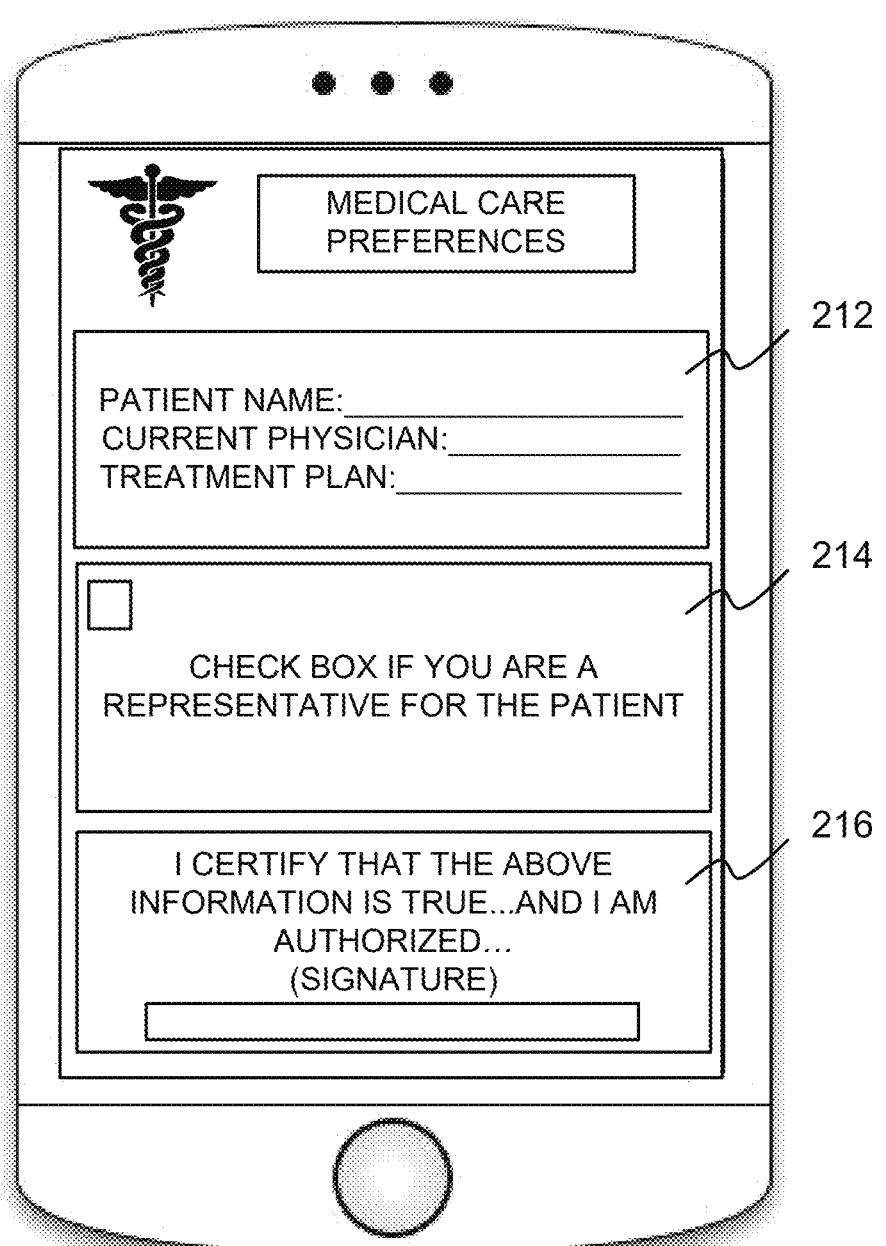
FIG. 2A illustrates a user interface of a personal computing device accessing the medical care service application according to an example embodiment.

FIG. 2A illustrates a user interface of a personal computing device accessing the medical care service application according to an example embodiment. Referring to FIG. 2A, the user interface 200 includes a set of setup information 212 and authorization information 214/216 which must be input to the interface in order to establish a working patient file for the health care service application. The patient may enter the information or the caregiver depending on the situation.

Figure 2B:
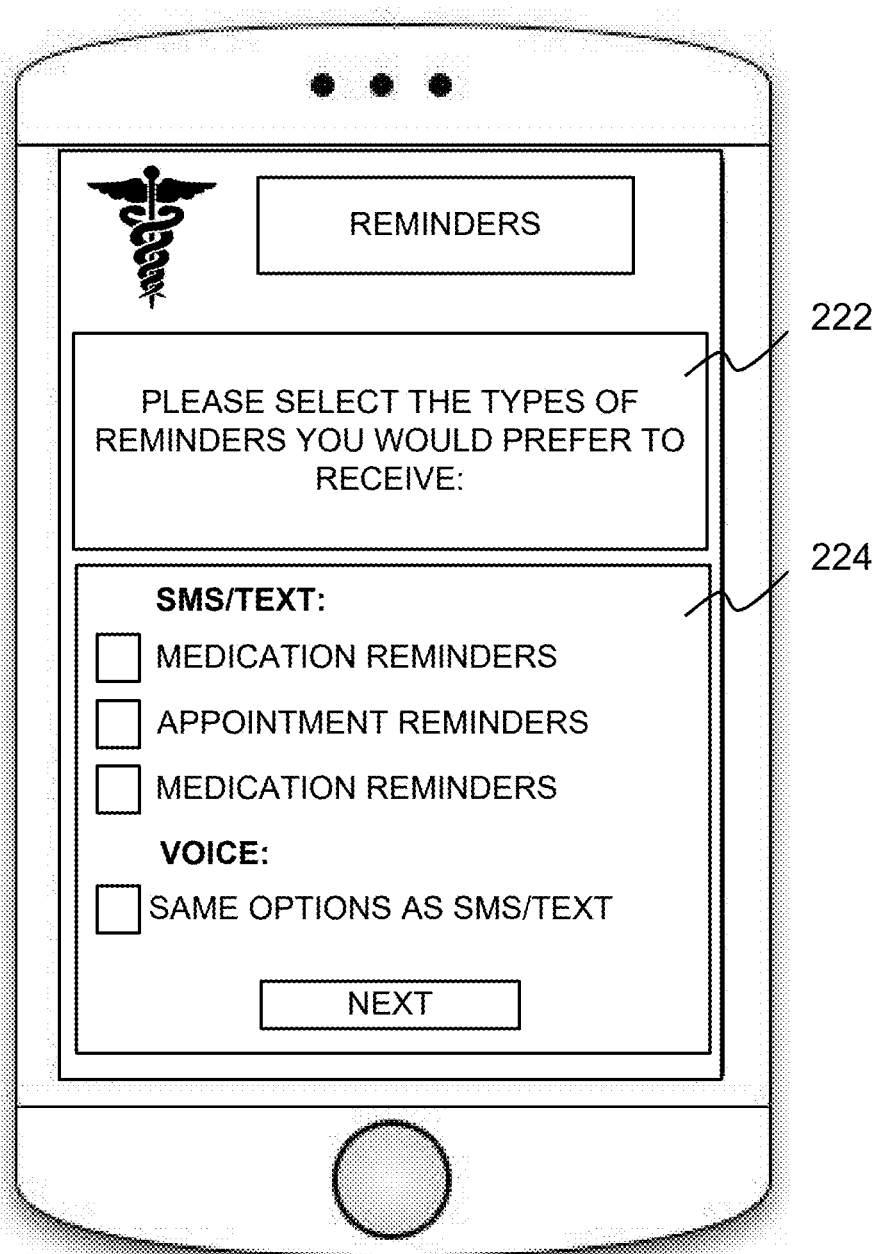
FIG. 2B illustrates a user interface of a personal computing device accessing a reminder configuration of the medical care service application according to an example embodiment.

FIG. 2B illustrates a user interface of a personal computing device accessing a reminder configuration of the medical care service application according to an example embodiment. Referring to FIG. 2B, the setup 220 may provide selecting a specific reminder preference/medium 222. This may include types of reminders 224 for a particular medium (i.e., SMS, email, IVR, etc.).

Figure 2C:
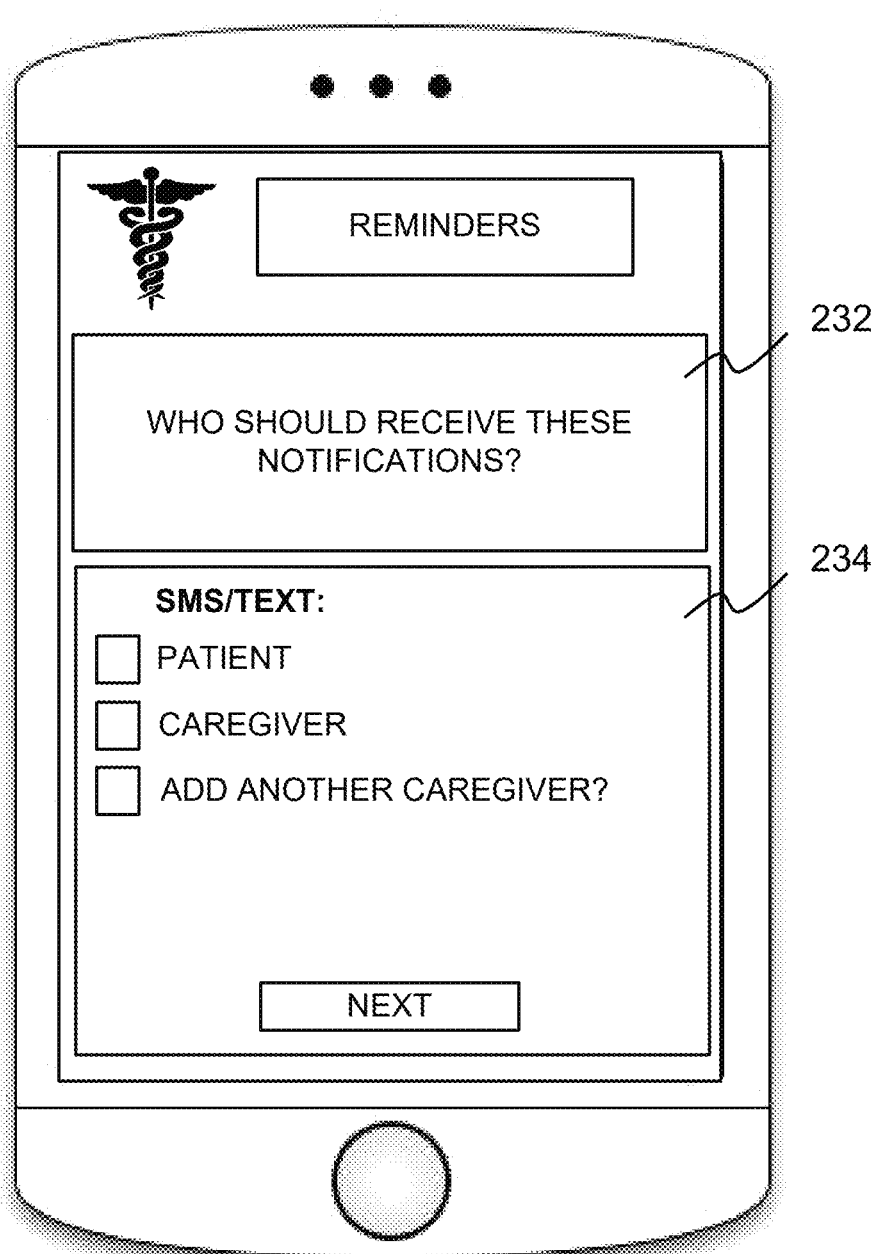
FIG. 2C illustrates a user interface of a personal computing device accessing a third party setup function of the medical care service application according to an example embodiment.

FIG. 2C illustrates a user interface of a personal computing device accessing a third party setup function of the medical care service application according to an example embodiment. Referring to FIG. 2C, the third parties may be setup 230 as one or more parties to receive the notification 232, such as emergency contacts, family, caregivers, etc. The individuals may be selected by category 234 to receive the notifications.

Figure 2D:
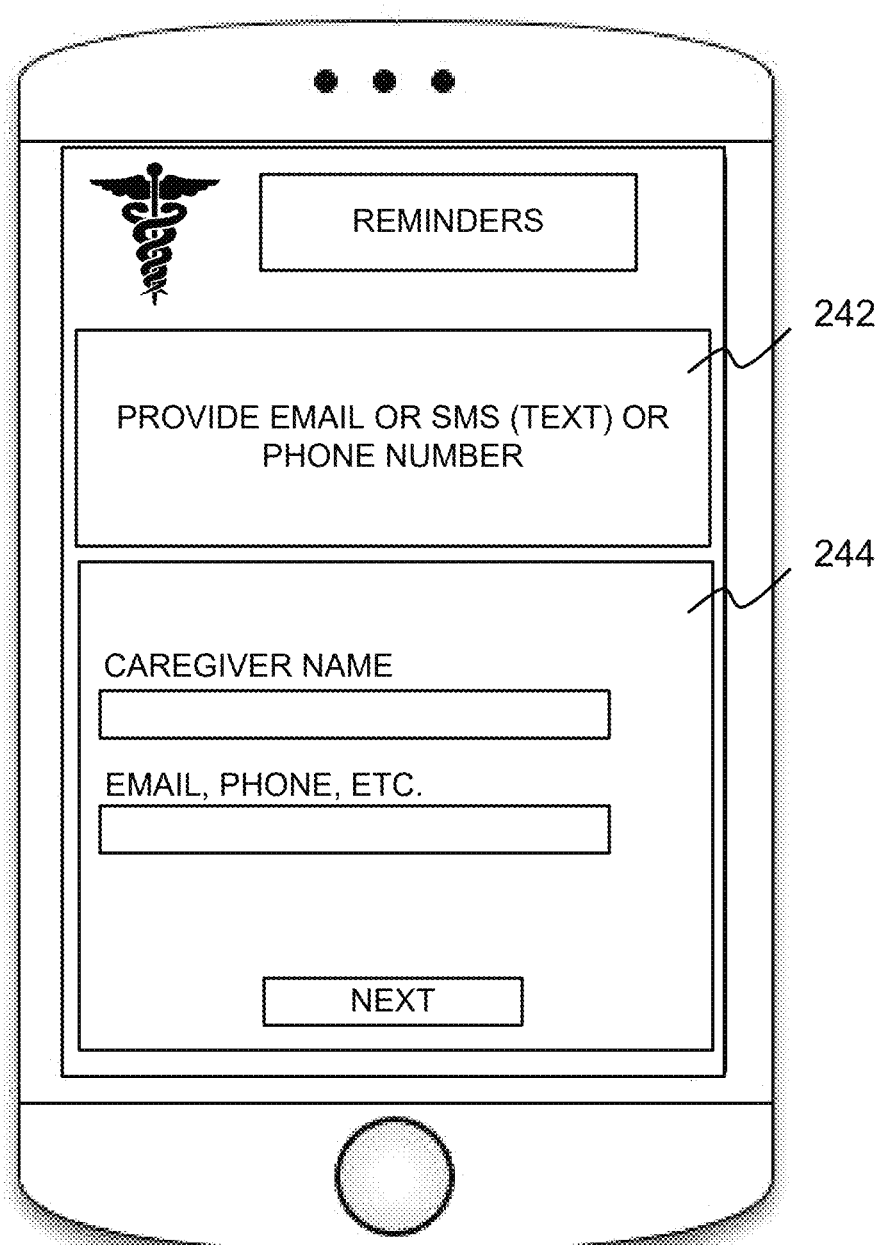
FIG. 2D illustrates another user interface of a personal computing device accessing a third party setup function of the medical care service application according to an example embodiment.

FIG. 2D illustrates another user interface of a personal computing device accessing a third party setup function of the medical care service application according to an example embodiment. Referring to FIG. 2D, the interface 240 includes additional examples of contact information and preferences 242 being submitted to the application for subsequent communication and monitoring. The caregivers may also be identified 244 for ease of use and continued health care services.

Figure 2E:
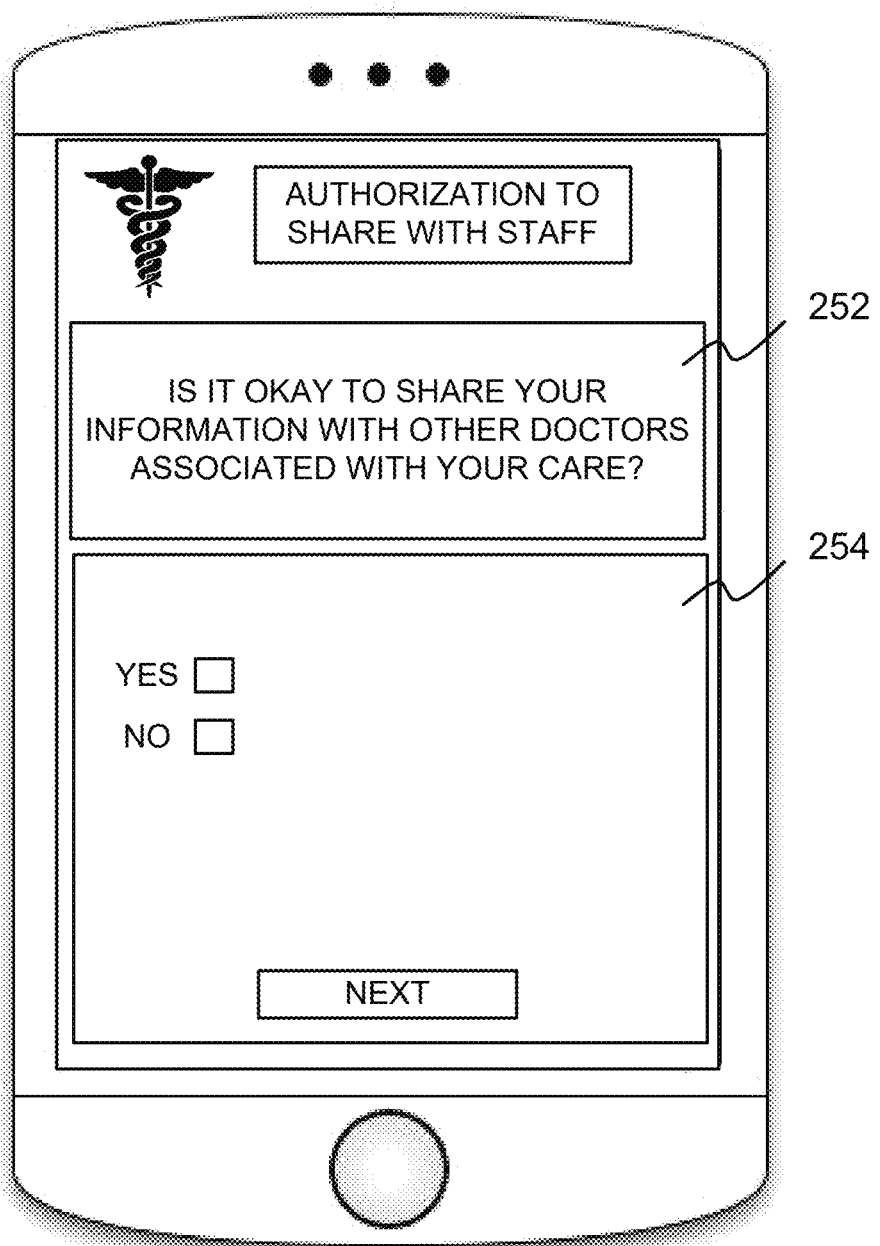
FIG. 2E illustrates a user interface of a personal computing device establishing a share function of the medical care service application according to an example embodiment.

FIG. 2E illustrates a user interface of a personal computing device establishing a share function of the medical care service application according to an example embodiment. Referring to FIG. 2E, the interface 250 includes an authorization option 252 and confirmation page 254 to ensure the HIPPA rules and regulations are observed for patient information security.

Figure 2F:
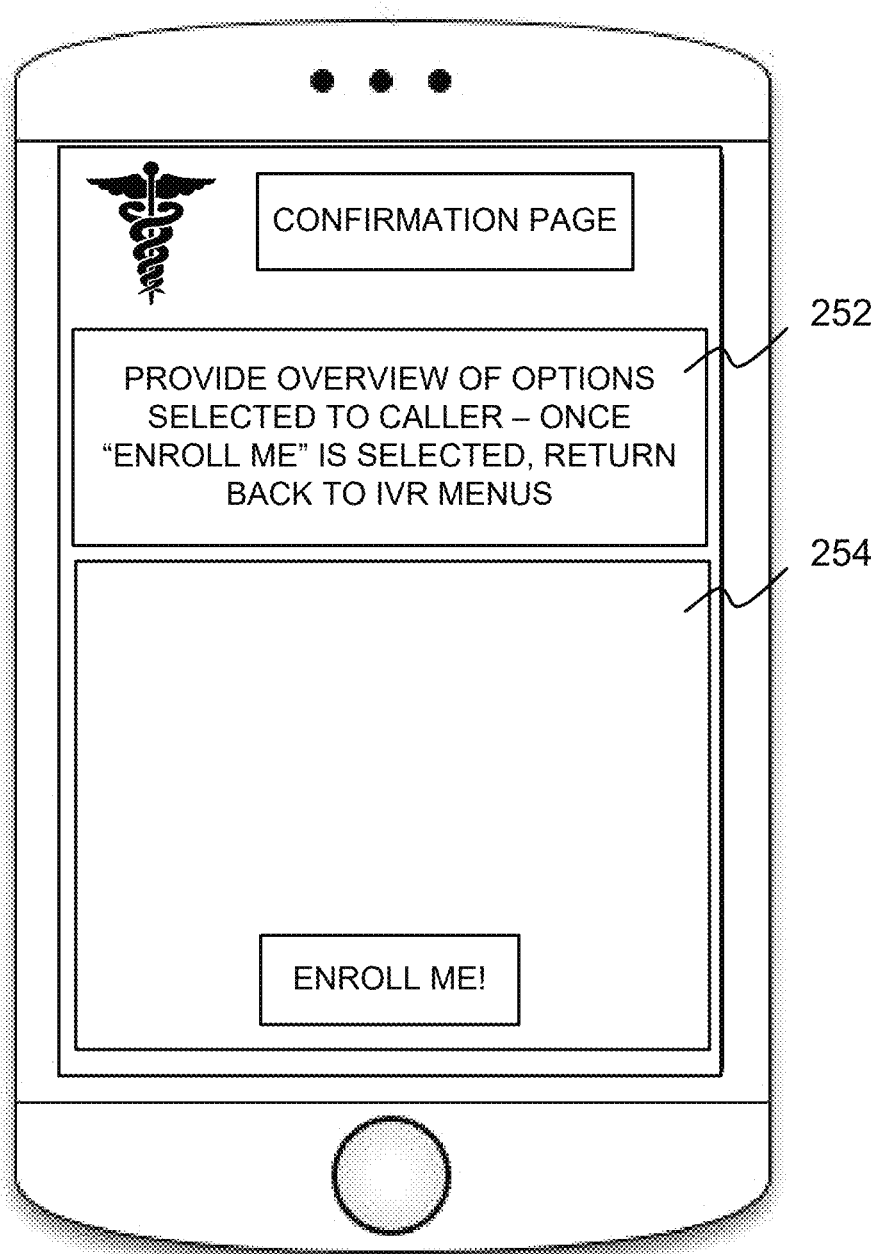
FIG. 2F illustrates a user interface of a personal computing device accessing a finalization menu of the medical care service application according to an example embodiment.

FIG. 2F illustrates a user interface of a personal computing device accessing a finalization menu of the medical care service application according to an example embodiment. Referring to FIG. 2F, the last interface 250 in this example setup procedure may include a confirmation page with the option to elect to 252 receive various enrollment information and other setup options for caregiver/patient care options and continued support 254.

Figure 3:
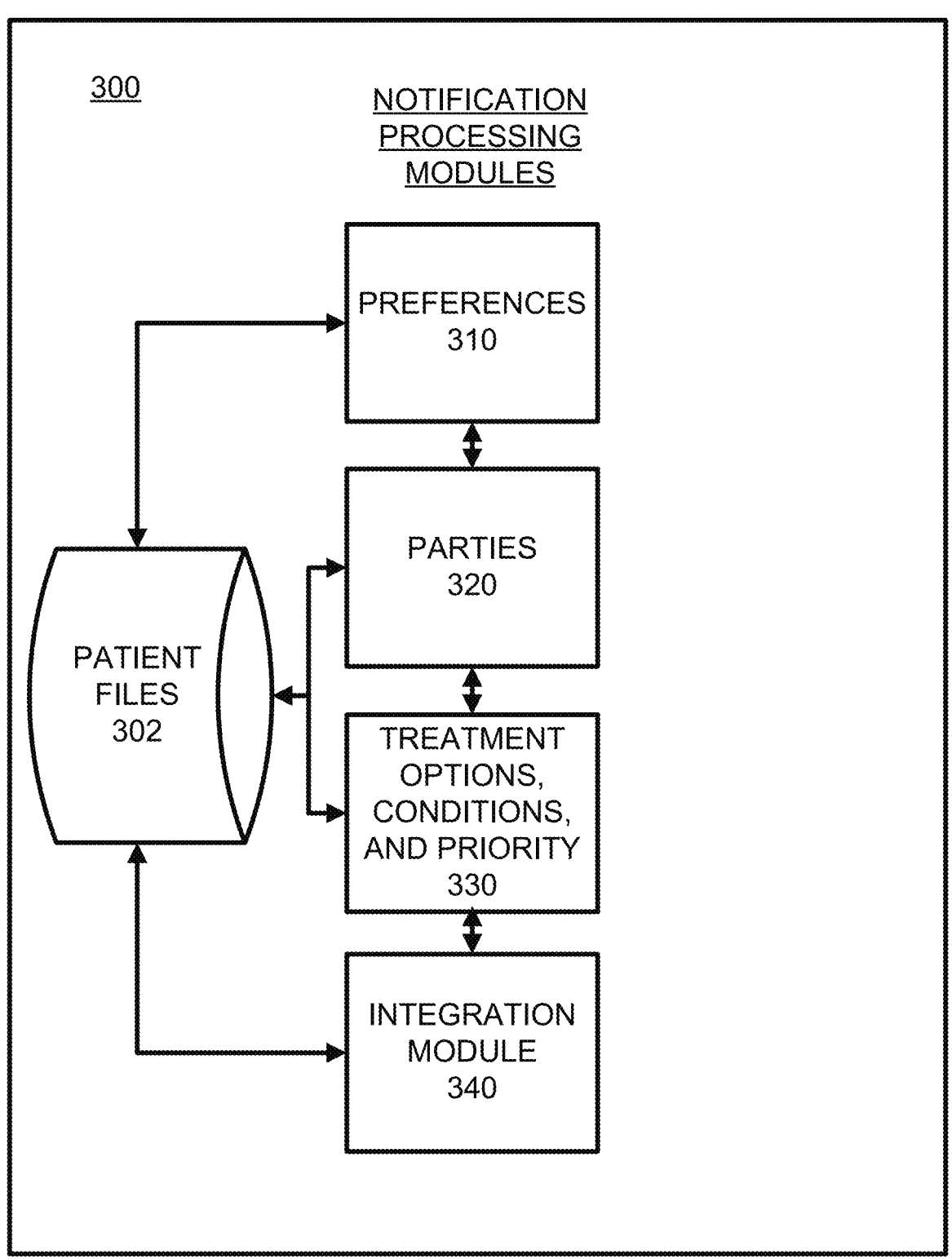
FIG. 3 illustrates logic module configuration for establishing patient care profiles according to an example embodiment.

FIG. 3 illustrates a logic module configuration for establishing patient care profiles according example embodiment. Referring to FIG. 3, in operation, the application may receive a flag to initiate a communication procedure. The procedure may include various modules integrated into the patient and caregiver communication process and also third party communication setup. For example, the patient files 302 may include a flag to initiate procedures for a follow-up appointment following a recent surgical procedure. The process 300 may include identifying a date that a follow-up should occur or a threshold by which the follow-up must occur. The patient's profile 302 is compared to the flag and preferences 310, parties 320, treatment options, conditions, priority status 330 (i.e., old vs. young, chronic health condition vs. healthy patient), may all be identified and used to customize the communication notifications and automated actions necessary to fulfill the flag requirements. The integration module may receive all the information and create notifications by linking origination information, destination information, communication medium preferences, etc. The result may be a number of notifications being sent to a number of different devices. The notifications may be labeled as having a particular status. For example, the notifications to the physicians may require feedback within a threshold time including advice, appointment dates, recommendations, etc. The status of those notifications may be an elevated severity status. The status of a notification to a caregiver may be non-elevated since the appointment does not require action by the caregiver and is sent merely as a reminder or status update. Notifications to a primary caregiver or the patient may be elevated since someone must take responsibility for ensuring the patient's compliance with the follow-up appointment.

Figure 4:
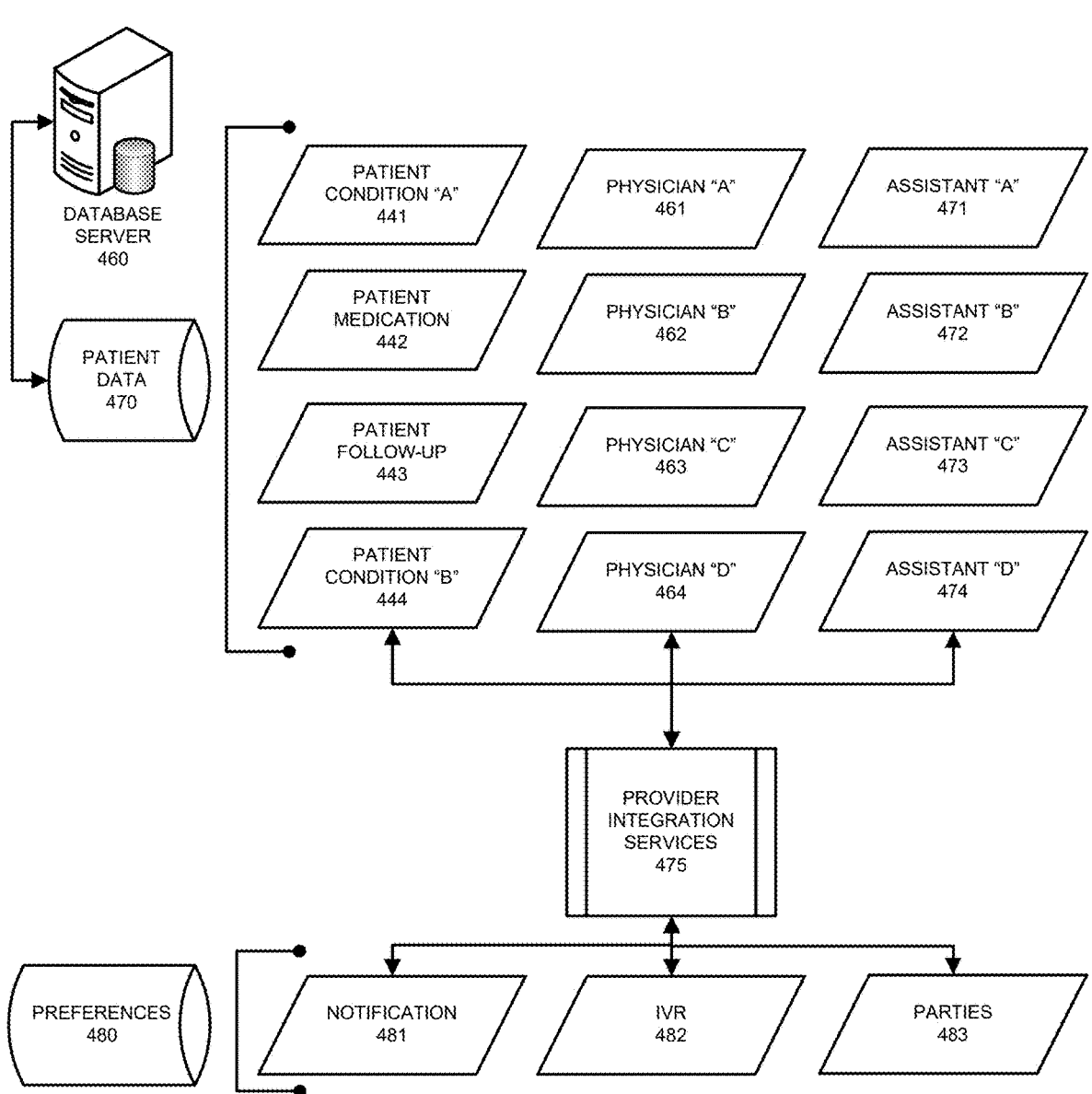
FIG. 4 illustrates a patient care data element selection and integration configuration according to an example embodiment.

FIG. 4 illustrates a patient care data element selection and integration configuration according to an example embodiment. Referring to FIG. 4, the data elements of the care application system 440 may include various entities as possible data selections for a particular action scenario. For instance, the patient file flag [F] of a particular file stored in the patient data 470 of the server 460 may be for a particular session, appointment, requirement, etc., which invokes any of the data elements for the patient 441-444 depending on the patient's current status and conditions, and also includes the physicians assigned to the patient 461-464 or which are invoked by the requirements associated with the patient flag [F]. Also, other third parties may be invoked into the notification processing module, such as assistants 471-474, which may be specialists related to the physicians or caregivers/family members which are pre-registered and accessible to the service requirements. For example, a flag [F] may identify a procedure which requires not one but two different assistants due to the severity of the procedure. Also, three doctors may be necessary to visit the patient and perform post-operation analysis. The integration services 474 takes this information and retrieves the provider preferences so all parties are notified as desired. The preferences 480 include notifications 481, IVR may communications 482 and/or parties which are specifically named as required to participate.

Figure 5:
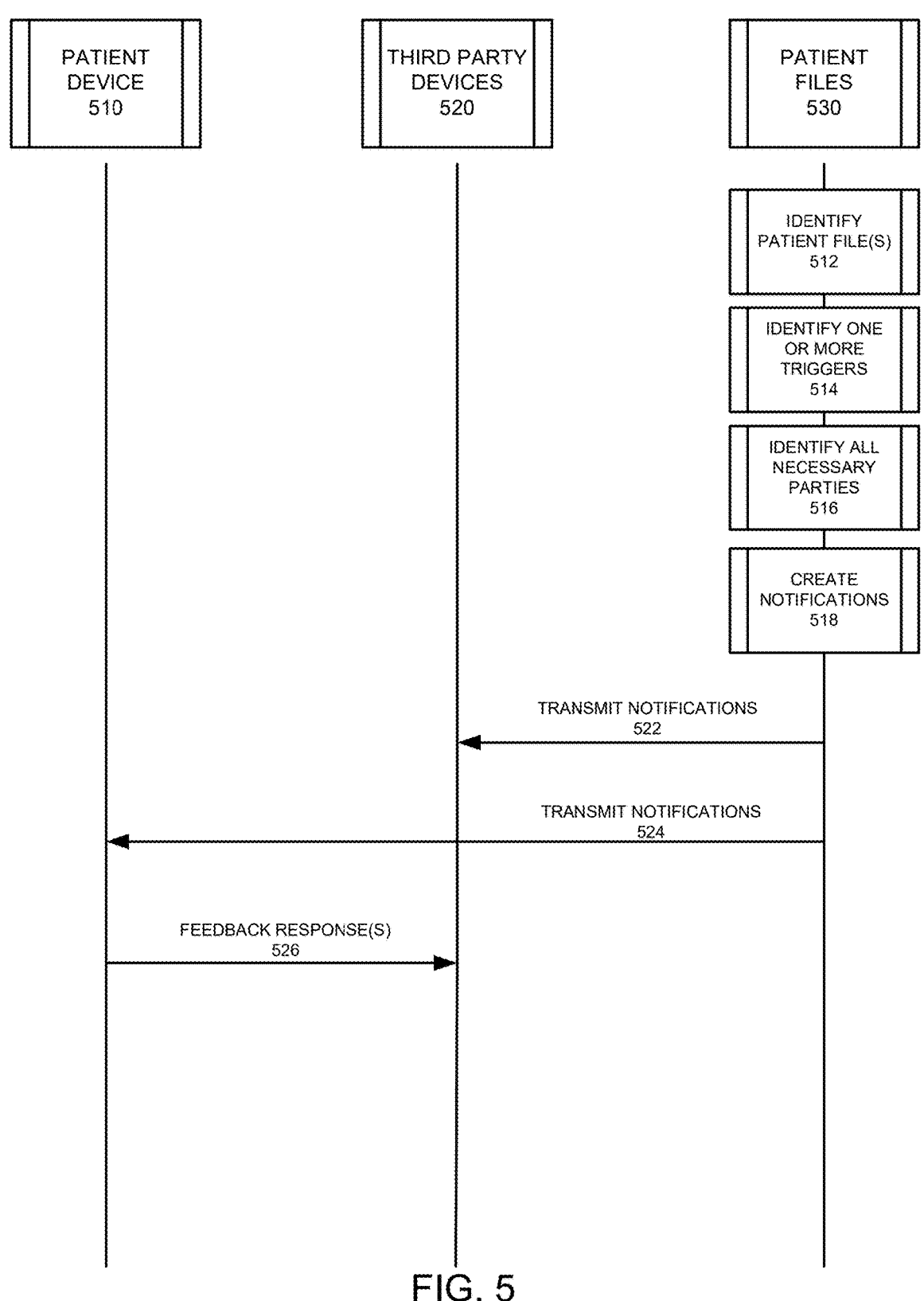
FIG. 5 illustrates a system signaling diagram of a patient care application procedure according to example embodiments.

FIG. 5 illustrates a system signaling diagram of patient care application procedure according to example embodiments. Referring to FIG. 5, the process 500 may include various communication entities, such as a patient communication device 510 and one or more third party devices 520. The patient data files may be stored in a remote server and referenced when necessary, such as when triggers require action, such as upcoming events, date deadlines, etc. One example method of operation may include identifying a patient case profile and identifying a plurality of contacts associated with the patient case profile 512. Next, the process includes identifying a trigger in the patient case file and a plurality of preferences 514. Triggers can include upcoming dates, important deadlines and requirements or other action creating instances. The process may also include linking a plurality of patient requirements identified in the patient case profile with the plurality of contacts and preferences responsive to identifying the trigger. The process further includes creating a plurality of communication instances each comprising at least one date and at least one communication medium for all parties 516, and transmitting notifications to the plurality of contacts 522 and at least one designated patient device 524 identified by the plurality of preferences.

The plurality of contacts include at least one emergency contact and at least one physician and the patient requirements include at least one medication, at least one follow-up communication with a physician among other requirements. The trigger includes a threshold date for a follow-up appointment or procedure, such as a deadline for patient care services. The communication instances include a plurality of different communication preferences identified via preferences for each of the plurality of contacts. The method may also include identifying an elevated severity level associated with one or more of the plurality of contacts. The method also provides creating at least one notification requiring a response based on the elevated severity level. The feedback to the severe notifications may be sent 526 to include confirmations and other responses to the severe concerns.

Another example embodiment may include a method that includes identifying a trigger in a patient case file associated with a patient that matures on a particular date, identifying a plurality of contacts required to satisfy the trigger, creating a plurality of communication instances each comprising at least one communication medium based on one or more preferences associated with the plurality of contacts, and transmitting notifications to the plurality of contacts and at least one designated patient device identified by the plurality of preferences.

The particular date can include a threshold date by which a patient must have a follow-up consultation based on a previous procedure. The method may also include identifying a plurality of patient requirements including at least one medication and at least one follow-up communication with a physician required by the trigger. The trigger can also include a specific procedure required for the patient.

The above embodiments may be implemented in hardware, in a computer program executed by a processor, in firmware, or in a combination of the above. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 6 illustrates an example network element 600, which may represent any of the above-described network components, etc.

Figure 6:
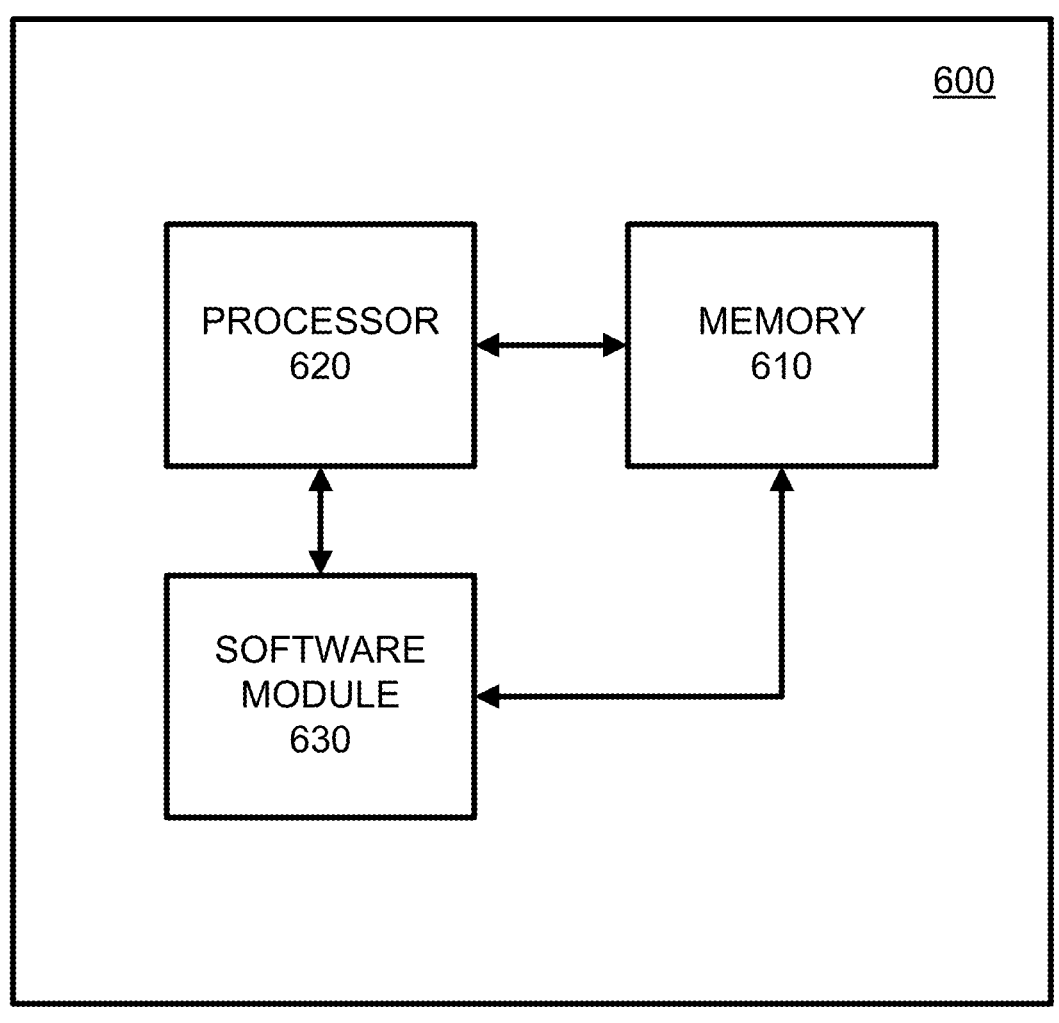
FIG. 6 illustrates a system network entity configured to store instructions and data necessary to perform and enact any of the enclosed embodiments.

As illustrated in FIG. 6, a memory 610 and a processor 620 may be discrete components of a network entity 600 that are used to execute an application or set of operations as described herein. The application may be coded in software in a computer language understood by the processor 620, and stored in a computer readable medium, such as, a memory 610. The computer readable medium may be a non-transitory computer readable medium that includes tangible hardware components in addition to software stored in memory. Furthermore, a software module 630 may be another discrete entity that is part of the network entity 600, and which contains software instructions that may be executed by the processor 620. In addition to the above noted components of the network entity 600, the network entity 600 may also have a transmitter and receiver pair configured to receive and transmit communication signals (not shown).

Although an exemplary embodiment of the system, method, and non-transitory computer readable medium has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way, but is intended to provide one example of many embodiments. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected single data set, or may be distributed over different including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed, but is merely representative of selected embodiments of the application.

One having ordinary skill in the art will readily understand that the above may be practiced with steps in a different order, and/or with hardware elements in configurations that are different than those which are disclosed.

Therefore, although the application has been described based upon these preferred embodiments, it would be apparent to those of skill in the art that certain modifications, variations, and alternative constructions would be apparent.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A method comprising:

enrolling a patient in a remote monitoring service by receiving input data, including preferences of a patient, via a plurality of screens sequentially displayed on a user interface;

storing enrollment data provided by the patient within a patient file stored in a storage device;

identifying a flag in the patient file, wherein the flag identifies requirements for a follow-up appointment for the patient;

determining contact information, a communication preference, a date parameter, and a physician of the patient from the requirements;

generating a plurality of electronic communications for a plurality of parties associated with the follow-up appointment, wherein each electronic communication of the plurality of electronic communications includes message content and contact information based on the requirements; and transmitting the plurality of electronic communications to a plurality of devices of the plurality of parties based on the requirements and at a time based on the requirements.

2. The method of claim 1, wherein the contact information identifies a plurality of contacts, including at least one emergency contact and the physician.

3. The method of claim 1, wherein the flag identifies at least one medication and at least one follow-up communication.

4. The method of claim 1, comprising:

identifying a threshold date for the follow-up appointment.

5. The method of claim 1, further comprising:

creating one or more notifications based on a severity level.

6. The method of claim 1, comprising:

identifying a procedure to be performed in the follow-up appointment and one or more assistants associated with the procedure.

7. An apparatus, comprising:

a processor that executes instructions stored in a memory to configure the processor to:

enroll a patient in a remote monitoring service based on input data, including preferences of a patient, received via a plurality of screens sequentially displayed on a user interface;

storing enrollment data provided by the patient within a patient file stored in a storage device;

identify a flag in the patient file, wherein the flag identifies requirements for a follow-up appointment for the patient;

determine contact information, a communication preference, a date parameter, and a physician of the patient from the requirements;

generate plurality of electronic communications for a plurality of parties associated with the follow-up appointment, wherein each electronic communication of the plurality of electronic communications includes message content and contact information based on the requirements; and transmit the plurality of electronic communications to a plurality of devices of the plurality of parties based on the requirements and at a time based on the requirements.

8. The apparatus of claim 7, wherein the contact information identifies a plurality of contacts, including at least one emergency contact and the physician.

9. The apparatus of claim 7, wherein the flag identifies at least one medication and at least one follow-up communication with a physician.

10. The apparatus of claim 7, wherein the processor is configured to:

identify a threshold date for the follow-up appointment.

11. The apparatus of claim 7, wherein the processor is configured to:

create one or more notifications based on a severity level.

12. A non-transitory computer-readable medium comprising at least one instruction that, when executed by a processor, causes the processor to perform:

enrolling a patient in a remote monitoring service by receiving input data, including preferences of a patient, via a plurality of screens sequentially displayed on a user interface;

storing enrollment data provided by the patient within a patient file stored in a storage device;

identifying a flag in the patient file, wherein the flag identifies requirements for a follow-up appointment for the patient;

determining contact information, a communication preference, a date parameter, and a physician of the patient from the requirements;

generating a plurality of electronic communications for a plurality of parties associated with the follow-up appointment, wherein each electronic communication of the plurality of electronic communications includes message content and contact information based on the requirements; and transmitting the plurality of electronic communications to a plurality of devices of the plurality of parties based on the requirements and at a time based on the requirements.

13. The non-transitory computer-readable medium of claim 12, wherein the contact information identifies a plurality of contacts, including at least one emergency contact and the physician.

14. The non-transitory computer-readable medium of claim 12, wherein the flag identifies at least one medication and at least one follow-up communication with a physician.

15. The non-transitory computer-readable medium of claim 12, wherein the instructions cause the processor to perform:

identifying a threshold date for the follow-up appointment.

16. The non-transitory computer-readable medium of claim 12, wherein the instructions cause the processor to perform:

creating one or more notifications based on a severity level.

* * * * *